US012597506B2

(12) United States Patent
Kimura et al.

(10) Patent No.: US 12,597,506 B2
(45) Date of Patent: Apr. 7, 2026

(54) ENDOSCOPIC EXAMINATION SUPPORT APPARATUS, ENDOSCOPIC EXAMINATION SUPPORT METHOD, AND RECORDING MEDIUM

(71) Applicant: NEC Corporation, Tokyo (JP)

(72) Inventors: Tatsu Kimura, Tokyo (JP); Takuma Igarashi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 145 days.

(21) Appl. No.: 18/528,922

(22) Filed: Dec. 5, 2023

(65) Prior Publication Data

US 2025/0182882 A1      Jun. 5, 2025

(51) Int. Cl.
| | |
|---|---|
| *G16H 30/40* | (2018.01) |
| *A61B 1/00* | (2006.01) |
| *G06T 7/00* | (2017.01) |
| *G06T 7/70* | (2017.01) |
| *G06T 11/00* | (2006.01) |
| *G06T 11/20* | (2006.01) |

(52) U.S. Cl.
CPC ....... *G16H 30/40* (2018.01); *A61B 1/000094* (2022.02); *A61B 1/000096* (2022.02); *A61B 1/0005* (2013.01); *G06T 7/0002* (2013.01); *G06T 7/70* (2017.01); *G06T 11/001* (2013.01); *G06T 11/206* (2013.01); *G06T 2207/10016* (2013.01); *G06T 2207/10024* (2013.01); *G06T 2207/10068* (2013.01); *G06T 2207/20081* (2013.01); *G06T 2207/30096* (2013.01)

(58) Field of Classification Search
CPC ............ G06T 2207/10068; G06T 2207/30096
USPC ......................................................... 345/589
See application file for complete search history.

(56) References Cited

U.S. PATENT DOCUMENTS

| | | | |
|---|---|---|---|
| 2016/0078620 A1 | 3/2016 | Iwanaka et al. | |
| 2021/0153808 A1 | 5/2021 | Tada et al. | |
| 2021/0161363 A1 | 6/2021 | Makino et al. | |
| 2021/0267544 A1* | 9/2021 | Saikou ................... | A61B 34/10 |
| 2021/0274999 A1* | 9/2021 | Kubota .............. | A61B 1/00045 |
| 2021/0280312 A1 | 9/2021 | Freedman et al. | |
| 2021/0383262 A1 | 12/2021 | Elen et al. | |
| 2021/0407077 A1* | 12/2021 | Makino ............ | A61B 1/000094 |

(Continued)

FOREIGN PATENT DOCUMENTS

| | | |
|---|---|---|
| JP | 7122328 B2 | 8/2022 |
| WO | 2019/155628 A1 | 8/2019 |

(Continued)

OTHER PUBLICATIONS

International Search Report for PCT Application No. PCT/JP2022/029104, mailed on Sep. 27, 2022.

(Continued)

*Primary Examiner* — Samantha (Yuehan) Wang
(74) *Attorney, Agent, or Firm* — Sughrue Mion, PLLC

(57) ABSTRACT

In the endoscopic examination support apparatus, the image acquisition means acquires an endoscopic video captured by an endoscope. The lesion detection means detects a lesion candidate from the endoscopic video. The heat map generation means generates a heat map indicating a possibility of lesion of the lesion candidate in the endoscopic video by a color. The display control means displays a position of a lesion on a frame of the endoscopic video based on the lesion candidate and the heat map.

11 Claims, 10 Drawing Sheets

100: ENDOSCOPIC EXAMINATION SYSTEM

(56) References Cited

U.S. PATENT DOCUMENTS

| | | |
|---|---|---|
| 2022/0020147 A1 | 1/2022 | Sasada et al. |
| 2022/0020496 A1 | 1/2022 | Saito et al. |
| 2022/0036542 A1 | 2/2022 | Sainz De Cea et al. |
| 2022/0148714 A1 | 5/2022 | Aisaka et al. |
| 2023/0255467 A1* | 8/2023 | Ikenoyama ........... G06T 7/0012 |
| | | 382/128 |
| 2024/0029404 A1 | 1/2024 | Watanabe |
| 2024/0037733 A1* | 2/2024 | Bang ...................... G06V 10/82 |
| 2024/0249409 A1 | 7/2024 | Mayer et al. |
| 2024/0324850 A1 | 10/2024 | Sasada et al. |

FOREIGN PATENT DOCUMENTS

| | | |
|---|---|---|
| WO | 2020/012530 A1 | 1/2020 |
| WO | 2020/110214 A1 | 6/2020 |
| WO | 2020/116115 A1 | 6/2020 |
| WO | 2020/121906 A1 | 6/2020 |
| WO | 2020/174863 A1 | 9/2020 |
| WO | 2020/195807 A1 | 10/2020 |
| WO | 2021/054477 A2 | 3/2021 |

OTHER PUBLICATIONS

JP Official Communication for JP Application No. 2024-536678, mailed on Aug. 26, 2025 with English Translation.
US Office Action for U.S. Appl. No. 18/525,167, mailed on Jun. 17, 2025.

* cited by examiner

100:ENDOSCOPIC EXAMINATION SYSTEM

ENDOSCOPIC EXAMINATION SUPPORT APPARATUS, ENDOSCOPIC EXAMINATION SUPPORT METHOD, AND RECORDING MEDIUM

CROSS REFERENCE TO RELATED APPLICATIONS

This application is a Continuation of U.S. application Ser. No. 18/286,636 filed Oct. 12, 2023, which is a National Stage of International Application No. PCT/JP2022/029104 filed Jul. 28, 2022, the contents of all of which are incorporated herein by reference in their entirety.

TECHNICAL FIELD

The present disclosure relates to processing of images relating to an endoscopic examination.

BACKGROUND ART

In the endoscopic examination, there is known a technology to detect lesion from the endoscopic image and superimpose figures or the like on the endoscopic image in order to indicate the position and size of the detected lesion. However, there is such a problem that the endoscopic image becomes difficult to see as a result of superimposing the figures. Patent Document 1 discloses a method of superimposing a marker surrounding the lesion on the observation image in accordance with the overlooking risk of the lesion when the lesion is detected, and a method of displaying a marker so as to surround the peripheral portion of the observation image.

PRECEDING TECHNICAL REFERENCES

Patent Document

Patent Document 1: International Publication WO2020/110214

SUMMARY

Problem to be Solved

However, even by Patent Document 1, it is not always possible to indicate the position and size of the lesion without superimposing figures or the like on the endoscopic image.

It is an object of the present disclosure to provide an endoscopic examination support apparatus that enables to grasp the position and size of a lesion.

Means for Solving the Problem

According to an example aspect of the present disclosure, there is provided an endoscopic examination support apparatus comprising:

a video acquisition means configured to acquire an endoscopic video captured by an endoscope;

a lesion detection means configured to detect a lesion candidate from the endoscopic video;

a heat map generation means configured to generate a heat map indicating a possibility of lesion of the lesion candidate in the endoscopic video by a color; and a display control means configured to display a position of a lesion on a frame of the endoscopic video based on the lesion candidate and the heat map.

According to another example aspect of the present disclosure, there is provided an endoscopic examination support method comprising:

acquiring an endoscopic video captured by an endoscope;

detecting a lesion candidate from the endoscopic video;

generating a heat map indicating a possibility of lesion of the lesion candidate in the endoscopic video by a color; and displaying a position of a lesion on a frame of the endoscopic video based on the lesion candidate and the heat map.

According to still another example aspect of the present disclosure, there is provided a recording medium storing a program, the program causing a computer to execute processing comprising:

acquiring an endoscopic video captured by an endoscope;

detecting a lesion candidate from the endoscopic video;

generating a heat map indicating a possibility of lesion of the lesion candidate in the endoscopic video by a color; and displaying a position of a lesion on a frame of the endoscopic video based on the lesion candidate and the heat map.

Effect

According to the present disclosure, a part of the endoscopic image is not blocked and the position and size of a lesion can be grasped.

EXAMPLE EMBODIMENTS

Preferred example embodiments of the present invention will be described with reference to the accompanying drawings.

First Example Embodiment

[System Configuration]

Figure 1:
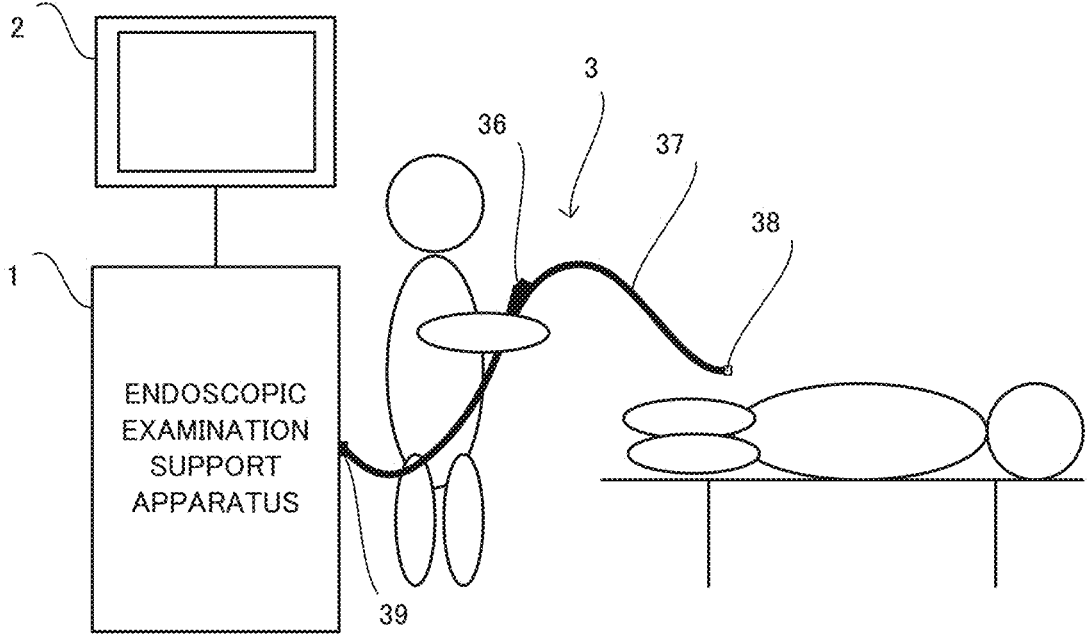
FIG. 1 is a block diagram showing a schematic configuration of an endoscopic examination system.

FIG. 1 shows a schematic configuration of an endoscopic examination system 100. The endoscopic examination system 100 detects a lesion during examination (including treatment) utilizing the endoscope and displays an indicator indicating the position and size of the lesion on the frame of the display screen of the endoscopic image. This allows the doctor to ascertain the position and size of the lesion without blocking a portion of the endoscopic image.

As shown in FIG. 1, the endoscopic examination system 100 mainly includes an endoscopic examination support apparatus 1, a display device 2, and an endoscope 3 connected to the endoscopic examination support apparatus 1.

The endoscopic examination support apparatus 1 acquires a moving image (i.e., a video, hereinafter also referred to as an "endoscopic video Ic") captured by the endoscope 3 during the endoscopic examination from the endoscope 3 and displays display data for the check by the examiner of the endoscopic examination on the display device 2. Specifically, the endoscopic examination support apparatus 1 acquires a moving image of the colon captured by the endoscope 3 as an endoscopic video Ic during the endoscopic examination. The endoscopic examination support apparatus 1 extracts still images (frame images) from the endoscopic video Ic and detects a lesion using AI (Artificial Intelligence). In addition, when a lesion is detected from the frame image by the AI, the endoscopic examination support apparatus 1 generates a heat map based on the frame image. The endoscopic examination support apparatus 1 generates indicators indicating the position and size of the lesion from the heat map. Then, the endoscopic examination support apparatus 1 generates the display data including the endoscopic video Ic, the heat map, the indicator, and the like.

The display device 2 is a display or the like for displaying an image on the basis of the display signal supplied from the endoscopic examination support apparatus 1.

The endoscope 3 mainly includes an operation unit 36 used by an examiner to input instructions such as air supply, water supply, angle adjustment, and an image-capturing instruction, a shaft 37 having flexibility and inserted into an organ of a subject to be examined, a tip portion 38 with a built-in image-taking unit such as an ultra-compact imaging element, and a connection unit 39 for connection with the endoscopic examination support apparatus 1.

[Hardware Configuration]

Figure 2:
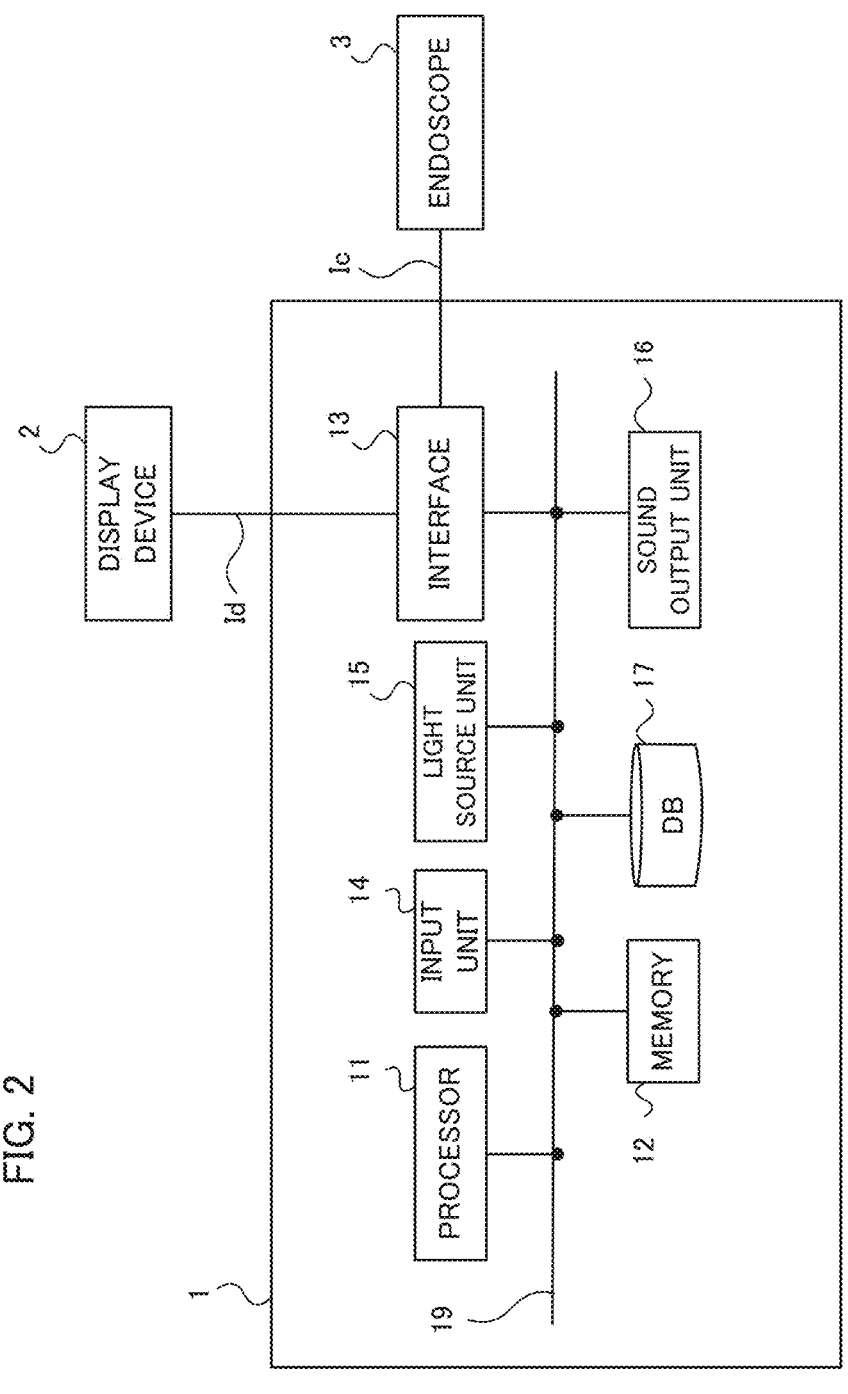
FIG. 2 is a block diagram showing a hardware configuration of an endoscopic examination support apparatus.

FIG. 2 shows a hardware configuration of the endoscopic examination support apparatus 1. The endoscopic examination support apparatus 1 mainly includes a processor 11, a memory 12, an interface 13, an input unit 14, a light source unit 15, a sound output unit 16, and a data base (hereinafter referred to as "DB") 17. Each of these elements is connected via a data bus 19.

The processor 11 executes a predetermined processing by executing a program stored in the memory 12. The processor 11 is a processor such as a CPU (Central Processing Unit), a GPU (Graphics Processing Unit), and a TPU (Tensor Processing Unit). The processor 11 may be configured by a plurality of processors. The processor 11 is an example of a computer.

The memory 12 is configured by various volatile memories used as a working memory and non-volatile memories for storing information needed for processing the endoscopic examination support apparatus 1, such as a RAM (Random Access Memory) and a ROM (Read Only Memory). Incidentally, the memory 12 may include an external storage device such as a hard disk connected to or incorporated in the endoscopic examination support apparatus 1, and may include a storage medium such as a removable flash memory or a disk medium. The memory 12 stores a program for the endoscopic examination support apparatus 1 to execute each process in the present example embodiment.

Also, the memory 12 temporarily stores a series of endoscopic videos Ic captured by the endoscope 3 in the endoscopic examination, based on the control of the processor 11. Further, the memory 12 temporarily stores the still images acquired from the endoscopic video Ic during endoscopic examination. These images are stored in the memory 12 in association with, for example, subject identification information (e.g., patient ID) and time stamp information, etc.

The interface 13 performs an interface operation between the endoscopic examination support apparatus 1 and the external devices. For example, the interface 13 supplies the display data Id generated by the processor 11 to the display device 2. Also, the interface 13 supplies the illumination light generated by the light source unit 15 to the endoscope 3. Also, the interface 13 supplies an electrical signal indicating the endoscopic video Ic supplied from the endoscope 3 to the processor 11. The interface 13 may be a communication interface such as a network adapter for wired or wireless communication with an external device, or may be a hardware interface compliant with a USB (Universal Serial Bus), SATA (Serial Advanced Technology Attachment), etc.

The input unit 14 generates an input signal based on the operation of the examiner. The input unit 14 is, for example, a button, a touch panel, a remote controller, a voice input device, or the like. The light source unit 15 generates the light to be delivered to the tip portion 38 of the endoscope 3. The light source unit 15 may also incorporate a pump or the like for delivering water or air to be supplied to the endoscope 3. The sound output unit 16 outputs the sound based on the control of the processor 11.

The DB 17 stores the endoscopic images acquired by past endoscopic examinations of the subject, and the lesion information. The lesion information includes a lesion image and related information. The lesion includes a polyp (protruding lesion). The DB 17 may include an external storage device, such as a hard disk connected to or incorporated in the endoscopic examination support device 1, and may include a storage medium, such as a removable flash memory. Instead of providing the DB 17 in the endoscopic examination system 100, the DB 17 may be provided in an external server or the like to acquire the lesion information from the server through communication.

[Functional Configuration]

Figure 3:
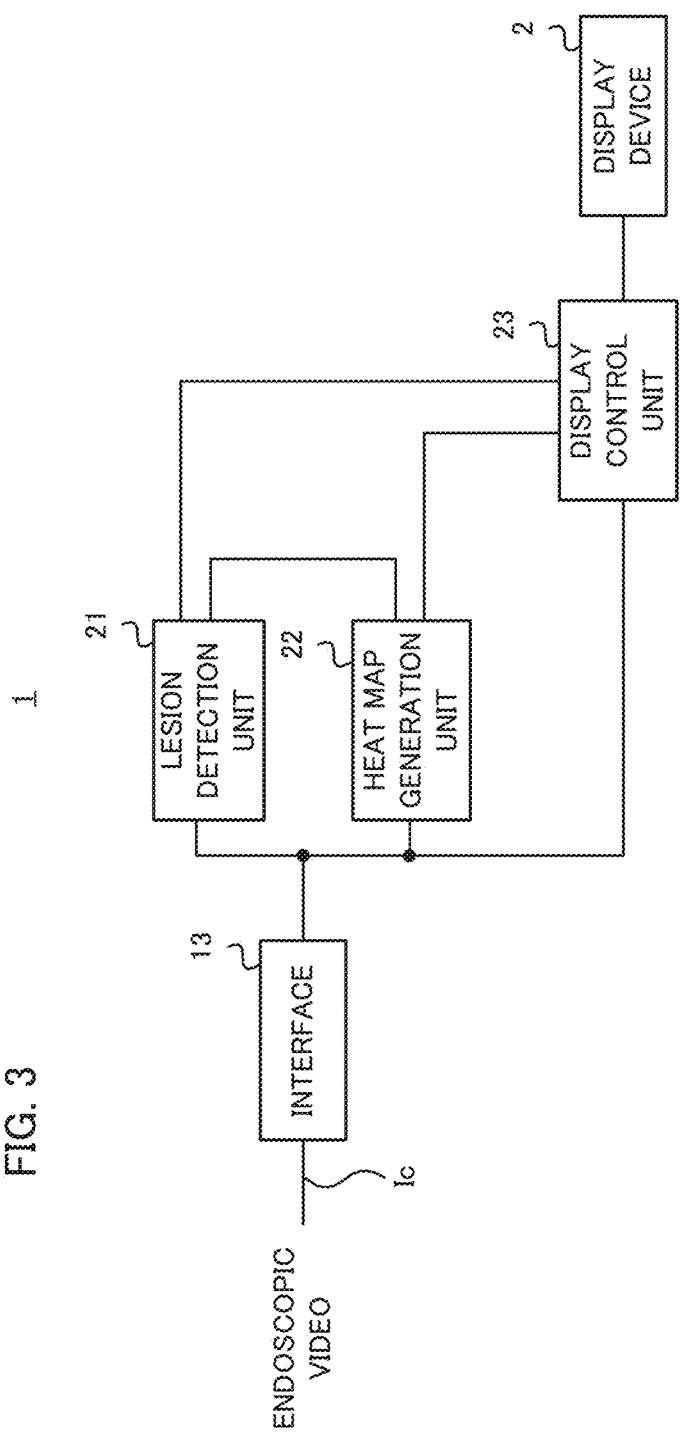
FIG. 3 is a block diagram showing a functional configuration of an endoscopic examination support apparatus.

FIG. 3 is a block diagram showing a functional configuration of the endoscopic examination support apparatus 1. The endoscopic examination support apparatus 1 functionally includes the interface 13, a lesion detection unit 21, a heat map generation unit 22, and a display control unit 23.

To the endoscopic examination support apparatus 1, the endoscopic video Ic is inputted from the endoscope 3. The endoscopic video Ic is inputted to the interface 13. The interface 13 extracts frame images (hereinafter, also referred to as "endoscopic images") from the inputted endoscopic video Ic and outputs the endoscopic images to the lesion detection unit 21 and the heat map generation unit 22. Also, the interface 13 outputs the inputted endoscopic video Ic to the display control unit 23.

The lesion detection unit 21 performs image analysis on the basis of the endoscopic images inputted from the interface 13 and determines whether or not a lesion is included in the endoscopic images. The lesion detection unit 21 detects a lesion-like portion (hereinafter, also referred to as a "lesion candidate") included in the endoscopic images using an image recognition model prepared in advance. This image recognition model is a model which is trained in advance so as to estimate the lesion candidate included in the endoscopic images, and is hereinafter referred to as a "lesion detection model". When the lesion candidate is detected, the lesion detection unit 21 outputs the determination result indicating the presence of the lesion to the heat map generation unit 22 and the display control unit 23 together with the information such as a time stamp. On the other hand, when the lesion is not detected, the lesion detection unit 21 outputs the determination result indicating the absence of the lesion to the heat map generation unit 22 and the display control unit 23.

The heat map generation unit 22 generates a heat map on the basis of the endoscopic images inputted from the interface 13 and the determination result inputted from the lesion detection unit 21.

Specifically, when the determination result indicating the presence of the lesion is inputted from the lesion detection unit 21, the heat map generation unit 22 acquires the endoscopic images including the lesion candidate from the endoscopic images inputted from the interface 13 on the basis of the information such as the time stamp. Then, the heat map generation unit 22 estimates whether or not the pixel is inside the area of the lesion candidate (hereinafter, also referred to as "the lesion area") for each pixel of the endoscopic image by using the image recognition model prepared in advance. This image recognition model is a model which is preliminarily trained to estimate whether or not a pixel is in the lesion area for each pixel of the endoscopic image, and is hereinafter also referred to as a "lesion score estimation model".

The heat map generation unit 22 estimates whether or not the pixel is in the lesion area for each pixel of the endoscopic image using the lesion score estimation model, and calculates a score (hereinafter, also referred to as "lesion score") indicating the probability that the pixel is in the lesion area. The lesion score is, for example, a value equal to or larger than 0 and equal to or smaller than 1. The closer to 1 the lesion score is, the higher the possibility that the pixel is in the lesion area is. Then, the heat map generation unit 22 generates a heat map based on the relationship between the predetermined lesion score and the color. The heat map generation unit 22 outputs the generated heat map to the display control unit 23.

In the above example, the heat map generation unit 22 generates a heat map when the determination result indicating the presence of the lesion is inputted from the lesion detection unit 21. However, the timing of generating the heat map is not limited to this example. For example, the heat map generation unit 22 may generate a heat map each time the endoscopic image is inputted from the interface 13 and output the heat map to the display control unit 23.

The display control unit 23 generates the display data based on the endoscopic video Ic inputted from the interface 13, the determination result inputted from the lesion detection unit 21, and the heat map inputted from the heat map generation unit 22, and outputs the display data to the display device 2.

Specifically, when the determination result indicating the presence of the lesion is inputted from the lesion detection unit 21, the display control unit 23 generates an indicator indicating the position and size of the lesion candidate based on the heat map. Then, the display control unit 23 includes the indicator in the display data, and outputs the display data to the display device 2. Further, when the determination result indicating the presence of the lesion is inputted successively a predetermined number of times from the lesion detection unit 21, the display control unit 23 regards that the lesion candidate is stably detected. Then, the display control unit 23 includes the endoscopic image and the heat map including the lesion candidate in the display data as the lesion history and the heat map corresponding to the lesion history described later, and outputs the display data to the display device 2. On the other hand, when the determination result indicating the absence of the lesion is inputted from the lesion detection unit 21, the display control unit 23 outputs the endoscopic video Ic as the display data to the display device 2.

Figure 4:
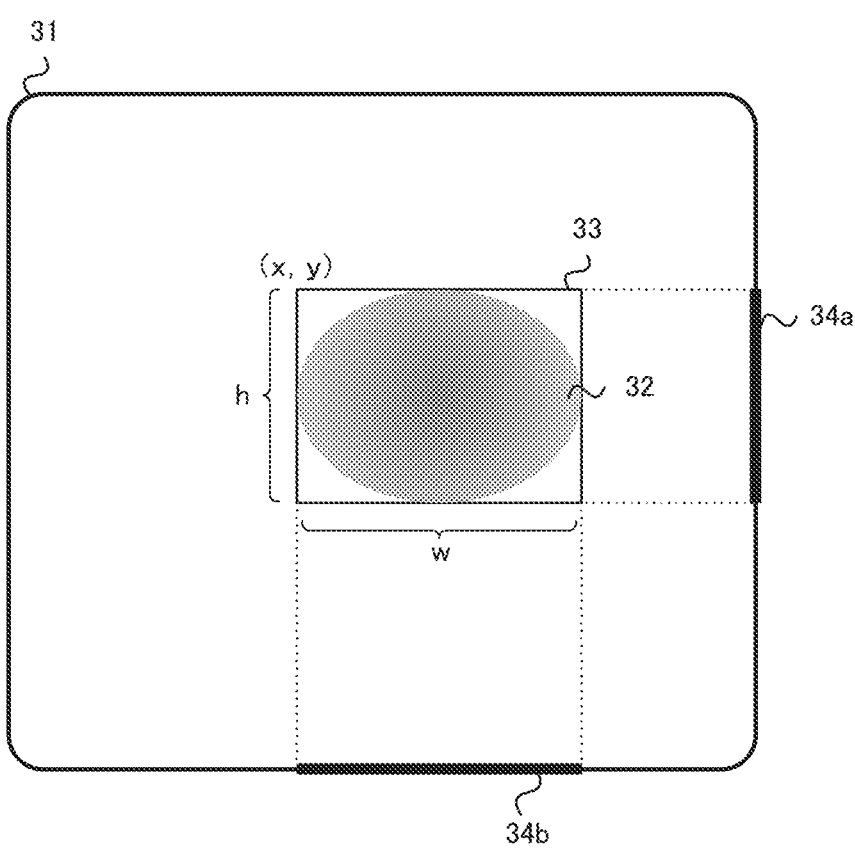
FIG. 4 is a diagram showing an example of a method of generating an indicator.

FIG. 4 is an example of a method of generating an indicator by the display control unit 23. In FIG. 4, a heat map 31, a lesion area 32, a rectangle 33, an indicator information 34*a*, and an indicator information 34*b* are shown.

The heat map 31 is the heat map inputted from the heat map generation unit 22. The lesion area 32 indicates the lesion candidate. The display control unit 23 compares the lesion score of each pixel of the heat map 31 with a predetermined threshold TH1, and sets the area formed by the pixels having the lesion score equal to or higher the threshold TH1 as the lesion area 32. The rectangle 33 is a rectangle surrounding the lesion area 32. The display control unit 23 surrounds the lesion area 32 with the rectangle 33, and generates coordinate information of the rectangle 33. For example, the coordinate information can be represented by the coordinates (x, y) of the upper left point of the rectangle 33, and the width w and height h of the rectangle 33 measured by using the upper left point as the origin. The display control unit 23 calculates the display position and size of the indicator (hereinafter, also referred to as indicator information) based on the coordinate information of the rectangle 33. Then, the display control unit 23 uses the calculation result to generate the indicator on the frame of the display screen of the endoscopic image and outputs the display data to the display device 2.

The display control unit 23 uses at least one of the left and right ends and at least one of the upper and lower ends of the display screen of the endoscopic image to generate an indicator by which the position and the size of the lesion candidate can be recognized. Therefore, the indicator information will be calculated in two places for one lesion area 32, like the indicator information 34*a* and 34*b* of FIG. 4.

In the above configuration, the interface 13 is an example of a video acquisition means, the lesion detection unit 21 is an example of a lesion detection means, the heat map generation unit 22 is an example of a het map generation means, the display control unit 23 is an example of a display control means.

[Display Example]

Next, a display example by the display device 2 will be described.

Figure 5:
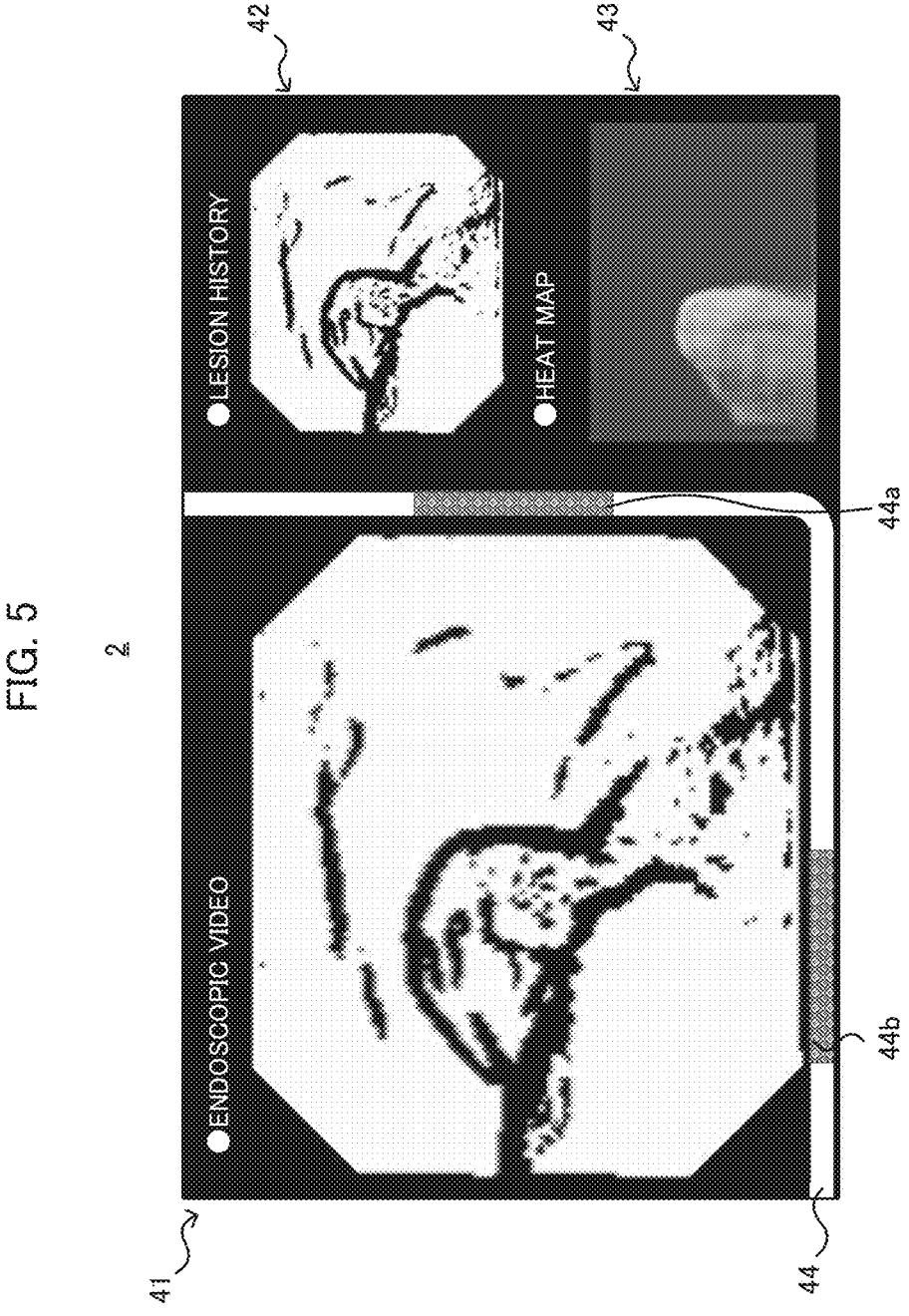
FIG. 5 is a diagram showing a display example of the endoscopic examination support apparatus.

FIG. 5 is an example of a display by the display device 2. In this example, the display device 2 displays an endoscopic video 41, a lesion history 42, a heat map 43, a display frame 44, and indicators 44*a* and 44*b*.

The endoscopic video 41 is the endoscopic video Ic captured during the endoscopic examination and updated as the endoscopic camera moves. The lesion history 42 is the endoscopic image that includes the lesion candidate detected during the endoscopic examination. If there are multiple endoscopic images including the lesion candidate, the endoscopic image including the most recent lesion candidate is displayed as the lesion history 42. The heat map 43 is the heat map of the endoscopic image corresponding to the lesion history 42.

The display screen frame 44 is a frame of the display screen of the endoscopic video 41. The indicators 44a and 44b are indicators that indicate the position and size of the lesion candidate. The indicator 44a and 44b are displayed on the display screen frame 44 when the lesion candidate is detected during endoscopic examination. The indicator 44a represents the longitudinal size and longitudinal position of the lesion candidate. The indicator 44b represents the lateral size and lateral position of the lesion candidate. By displaying the indicators 44a and 44b, the doctor can ascertain the position and size of the lesion candidate.

Figure 6:
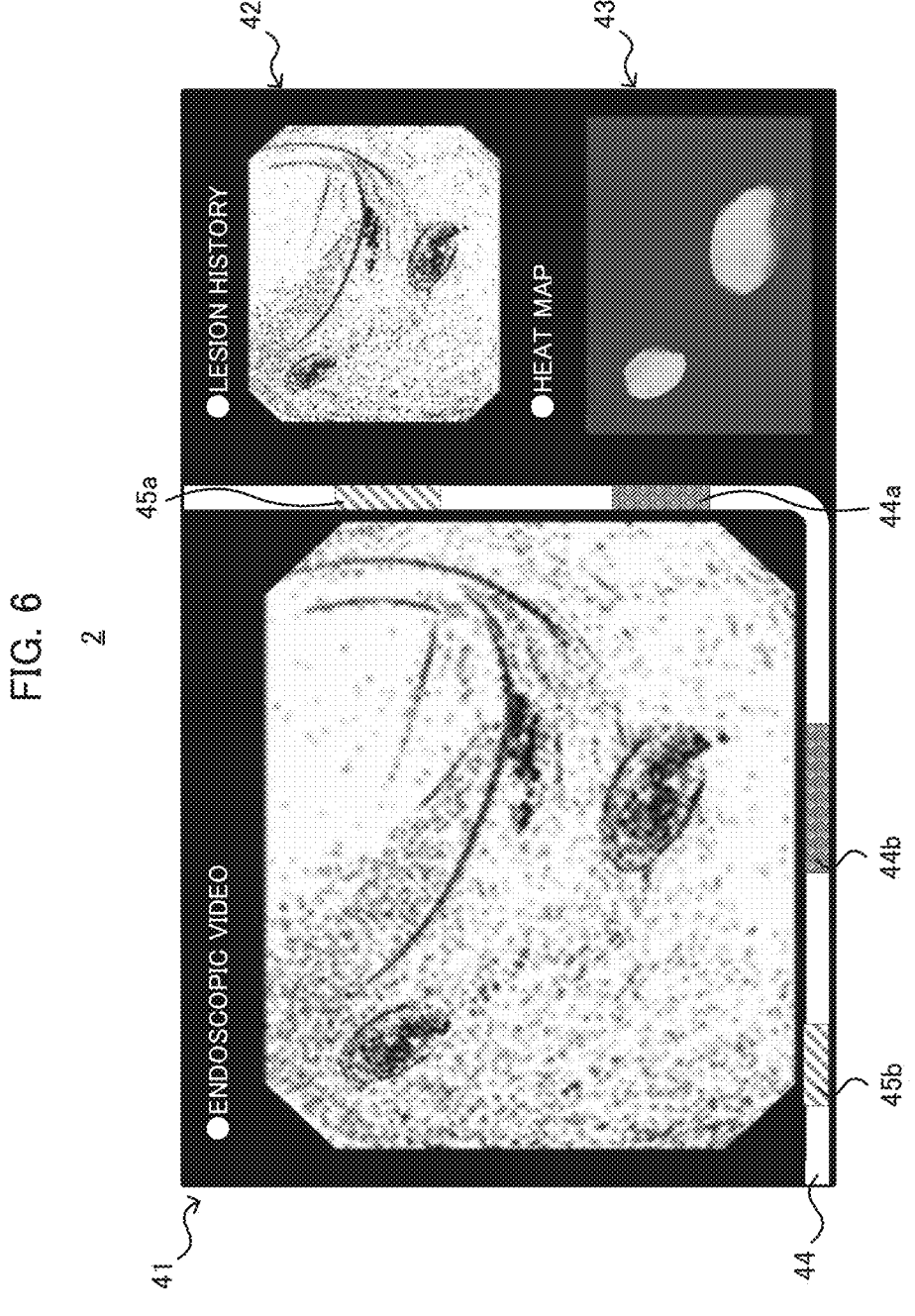
FIG. 6 is a diagram showing another display example of the endoscopic examination support apparatus.

FIG. 6 shows another display example by the display device 2. This example is directed to the case where two lesion candidates are detected. Specifically, in FIG. 6, the position and size of one lesion candidate is shown by the gray indicators 44a and 44b and the position and size of the other lesion candidate is shown by the diagonally-hatched indicators 45a and 45b. As shown in FIG. 6, by generating the indicators of different display mode for each of the lesion candidates and displaying them on the display screen frame 44, the doctor can grasp the position and size of each of the lesion candidates even when multiple lesion candidates are detected at the same time.

Figure 7:
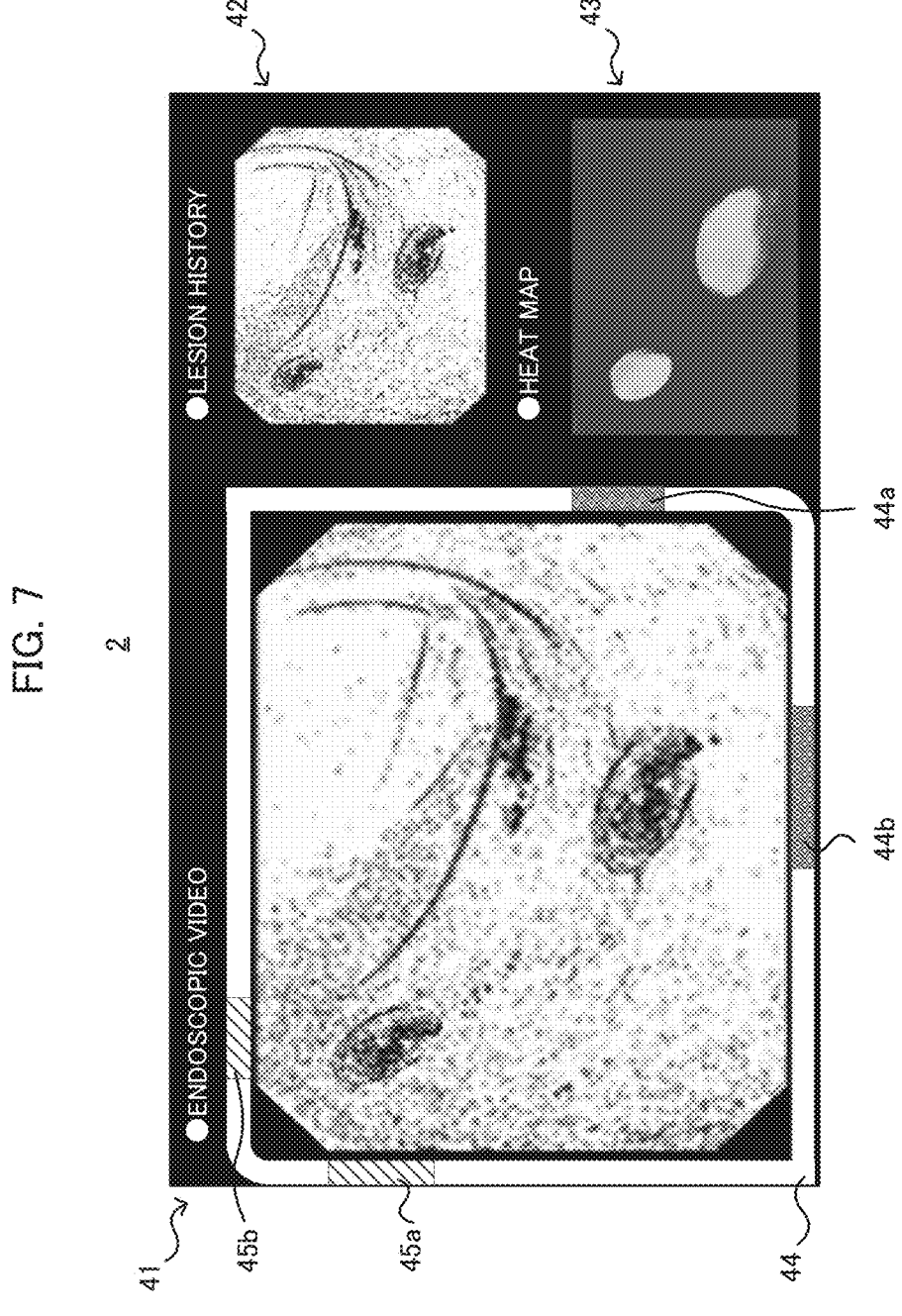
FIG. 7 is a diagram showing still another display example of the endoscopic examination support apparatus.

FIG. 7 shows still another display example by the display device 2. This example is directed to the case where two lesion candidates are detected. In FIG. 6, the indicators 44a and 44b and the indicators 45a and 45b are displayed at the lower and right ends of the endoscopic video 41. However, when multiple lesion candidates are detected, the indicators overlap depending on the positional relationship, making it difficult for the doctor to grasp the position and size of the lesion candidates. Therefore, in FIG. 7, the upper end and the left end of the endoscopic video 41 are used as display locations of the indicators in addition to the lower end and the right end of the endoscopic video 41. This makes it possible to prevent the indicators from being displayed in an overlapping manner when multiple lesion candidates are detected.

[Image Display Processing]

Figure 8:
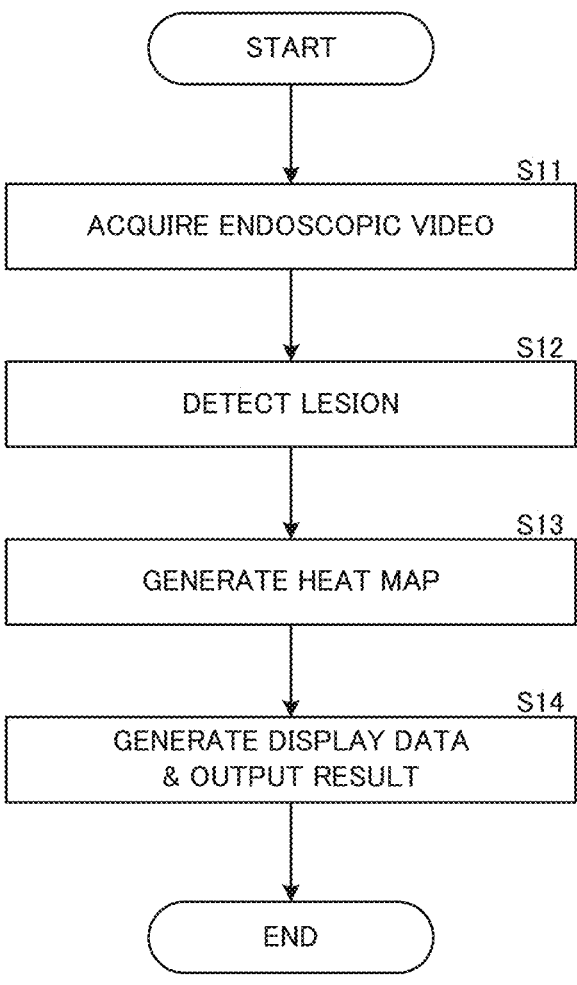
FIG. 8 is a flowchart of display processing by the endoscopic examination support apparatus.

Next, display processing for performing the above-mentioned display will be described. FIG. 8 is a flowchart of processing performed by the endoscopic examination support apparatus 1. This processing is realized by the processor 11 shown in FIG. 2, which executes a pre-prepared program and operates as the elements shown in FIG. 3.

First, the endoscopic video Ic is inputted from the endoscope 3 to the interface 13. The interface 13 acquires the endoscopic images from the inputted endoscopic video Ic (step S11). The interface 13 outputs the endoscopic images to the lesion detection unit 21 and the heat map generation unit 22. Further, the interface 13 outputs the endoscopic video Ic to the display control unit 23. Next, the lesion detection unit 21 detects the lesion from the endoscopic images (step S12). Specifically, the lesion detection unit 21 determines whether or not the lesion is included in the endoscopic images by using the lesion detection model. Then, the lesion detection unit 21 outputs the determination result to the heat map generation unit 22 and the display control unit 23.

Next, the heat map generation unit 22 generates a heat map from the endoscopic image when the lesion is detected (step S13). Specifically, the heat map generation unit 22 estimates the lesion score for each pixel of the endoscopic image using the lesion score estimation model. Then, the heat map generation unit 22 generates a heat map based on the relationship between the score and the color determined in advance. Then, the heat map generation unit 22 outputs the generated heat map to the display control unit 23.

Next, the display control unit 23 generates display data from the endoscopic image inputted from the interface 13, the determination result inputted from the lesion detection unit 21, and the heat map inputted from the heat map generation unit 22, and outputs the display data to the display device 2 (step S14). Incidentally, the display control unit 23 generates the indicators indicating the position and size of the lesion candidate if the endoscopic image includes the lesion candidate. Then, the display control unit 23 includes the indicators in the display data, and outputs the display data to the display device 2.

Modifications

Next, modifications of the first example embodiment will be described. The following modifications can be applied to the first example embodiment in appropriate combination.

Modification 1

In the first example embodiment described above, the indicator is represented by a single color. However, the display mode of the indicator may be changed according to the lesion score. Specifically, the display control unit 23 may change the display mode of the indicator according to the lesion scores of the pixels in the lesion area. For example, the display control unit 23 may add shading to the indicator. For example, if the central portion of the lesion area has a high lesion score and the lesion score decreases as the position moves away from the central portion of the lesion area, the display control unit 23 may darken the central portion of the indicator and lighten the other portions. Thus, by changing the display mode of the indicator, it is possible for the doctor to grasp the position of the more noteworthy lesion candidates.

Modification 2

The display control unit 23 may change the display mode of the indicator depending on the lesion score of the entire lesion area. Specifically, the display control unit 23 may calculate the average value of the lesion score allocated to each pixel of the lesion area (hereinafter, also referred to as "lesion area score.") and change the display mode of the indicator depending on the lesion area score. For example, the display control unit 23 sets the color of the indicator to red when the lesion area score is equal to or larger than the predetermined threshold TH2, and sets the color of the indicator to yellow when the lesion area score is smaller than the predetermined threshold TH2. In this way, the display mode of the indicators may be changed to attract the attention of the doctor for the lesion candidate having a high lesion area score.

Modification 3

In the above-described first example embodiment, when the lesion candidate is detected, the indicator is uniformly displayed. However, the display control unit 23 may display or hide the indicator depending on the lesion area score. For example, the display control unit 23 may display the indicator only when the lesion area score is equal to or larger than a predetermined threshold TH3.

Modification 4

In the above-described first example embodiment, the indicator is uniformly displayed when the lesion candidate is detected. However, the display control unit 23 may display or hide the indicator according to the size of the lesion candidate. For example, the display control unit 23 may display the indicator only when the area of the lesion candidate is equal to or larger than a predetermined threshold TH4.

Modification 5

The display mode of the indicator may be changed for each doctor. For example, the display location of the indicators may be selected from the left and right ends and the upper and lower ends for each doctor. Further, the color and/or pattern of the indicator may be selected for each doctor. Thus, it is possible to display the indicator in an easy-to-see display manner for each doctor.

Modification 6

In the above-described first example embodiment, the lesion detection unit 21 detects the lesion candidate. Instead, the heat map generation unit 22 may detect the lesion candidate. In this case, the heat map generation unit 22 performs image analysis on the basis of the endoscopic images inputted from the interface 13, and determines whether or not the endoscopic images include a lesion. Then, the heat map generation unit 22 generates a heat map when the endoscopic images include the lesion. Then, the heat map generation unit 22 inputs the determination result indicating the presence or absence of the lesion and the heat map to the display control unit 23. The lesion score estimation model used by the heat map generator 22 is a trained model which is trained to calculate the lesion score for each pixel of the endoscopic image and detect the lesion candidate.

Second Example Embodiment

Figure 9:
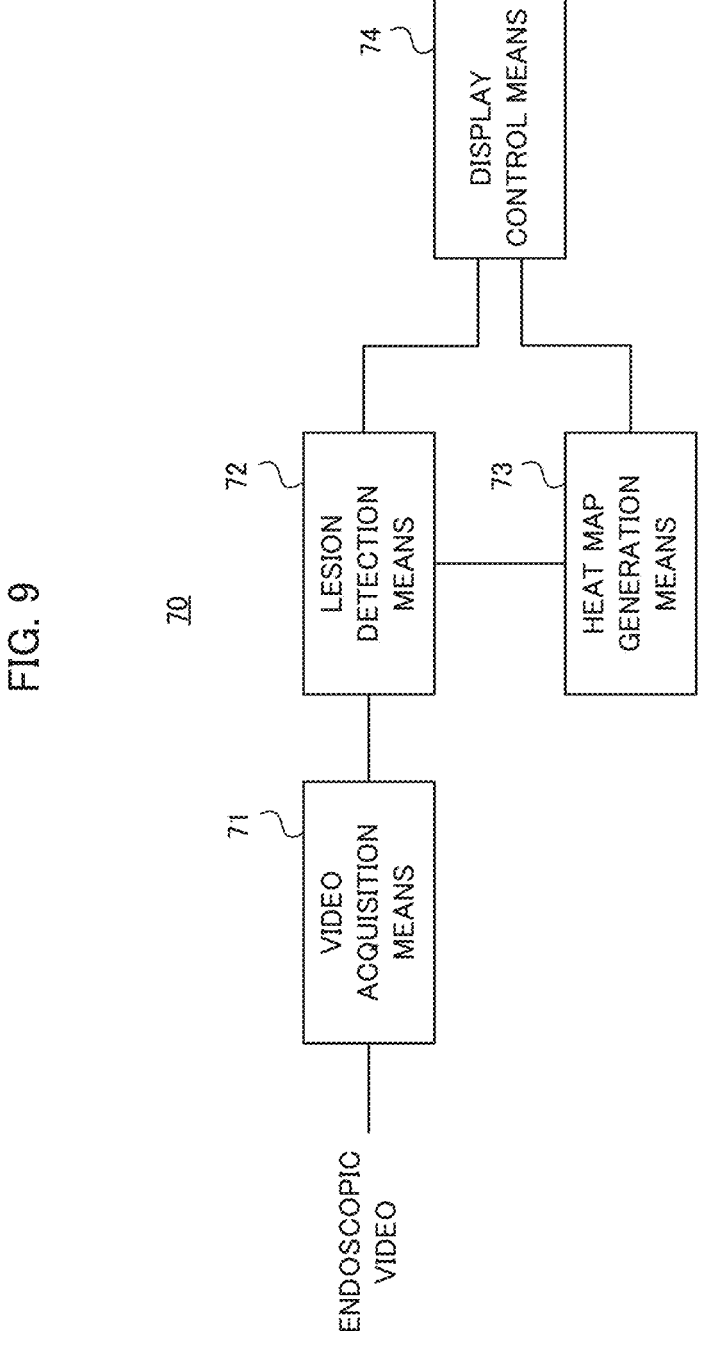
FIG. 9 is a block diagram showing a functional configuration of an endoscopic examination support apparatus of a second example embodiment.

FIG. 9 is a block diagram illustrating a functional configuration of an endoscopic examination support apparatus according to a second example embodiment. The endoscopic examination support apparatus 70 includes a video acquisition means 71, a lesion detection means 72, a heat map generation means 73, and a display control means 74.

Figure 10:
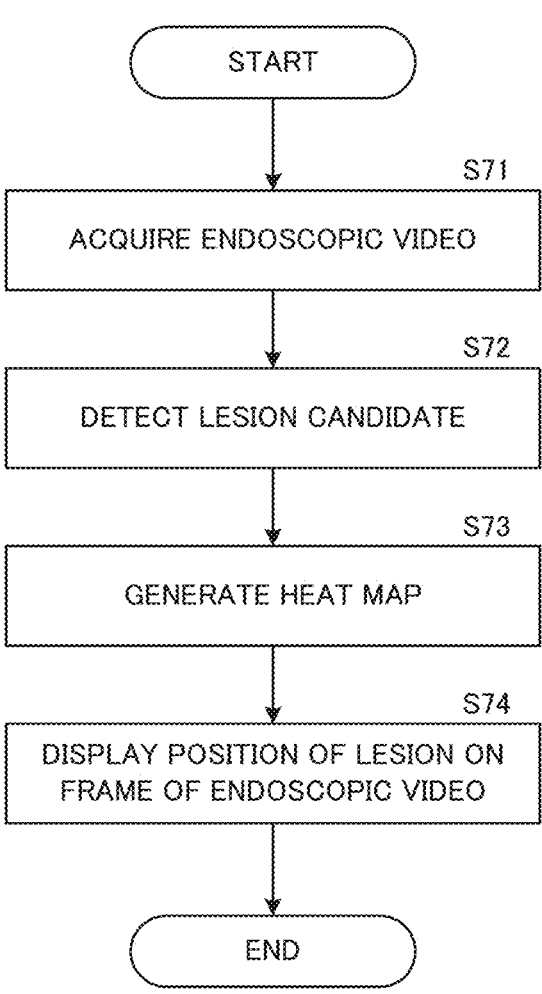
FIG. 10 is a flowchart of processing by the endoscopic examination support apparatus of the second example embodiment.

FIG. 10 is a flowchart of processing performed by the endoscopic examination support apparatus according to the second example embodiment. The the image acquisition means 71 acquires an endoscopic video captured by an endoscope (step S71). The lesion detection means 72 detects a lesion candidate from the endoscopic video (step S72). The heat map generation means 73 generates a heat map indicating a possibility of lesion of the lesion candidate in the endoscopic video by a color (step S73). The display control means 74 displays a position of a lesion on a frame of the endoscopic video based on the lesion candidate and the heat map (step S74).

While the present disclosure has been described with reference to the example embodiments and examples, the present disclosure is not limited to the above example embodiments and examples. Various changes which can be understood by those skilled in the art within the scope of the present disclosure can be made in the configuration and details of the present disclosure.

Supplementary Note 1

An endoscopic examination support apparatus comprising:
 a video acquisition means configured to acquire an endoscopic video captured by an endoscope;
 a lesion detection means configured to detect a lesion candidate from the endoscopic video;
 a heat map generation means configured to generate a heat map indicating a possibility of lesion of the lesion candidate in the endoscopic video by a color; and
 a display control means configured to display a position of a lesion on a frame of the endoscopic video based on the lesion candidate and the heat map.

Supplementary note 2

The endoscopic examination support apparatus according to Supplementary note 1, wherein the heat map generation means represents the possibility of lesion by a score for each pixel included in a frame image of the endoscopic video, and wherein the display control means displays the position of the lesion on the frame of the endoscopic video in a display mode according to the score.

Supplementary note 3

The endoscopic examination support apparatus according to Supplementary note 1,
 wherein the heat map generation means represents the possibility of lesion by a score for each pixel included in a frame image of the endoscopic video, and
 wherein the display control means calculates an average value of the scores and displays the position of the lesion on the frame of the endoscopic video in a display mode according to the average value.

Supplementary note 4

The endoscopic examination support apparatus according to Supplementary note 1,
 wherein the heat map generation means represents the possibility of lesion by a score, and
 wherein the display control means displays the position of the lesion on the frame of the endoscopic video when the score is equal to or larger than a predetermined threshold value.

Supplementary note 5

The endoscopic examination support apparatus according to Supplementary note 1, wherein, when the lesion detection means detects multiple lesion candidates, the display control means displays the positions of the multiple lesion candidates on the frame of the endoscopic video in different display modes.

Supplementary note 6

An endoscopic examination support method comprising:
 acquiring an endoscopic video captured by an endoscope;
 detecting a lesion candidate from the endoscopic video;

generating a heat map indicating a possibility of lesion of the lesion candidate in the endoscopic video by a color; and displaying a position of a lesion on a frame of the endoscopic video based on the lesion candidate and the heat map.

Supplementary note 7

A recording medium storing a program, the program causing a computer to execute processing comprising:

acquiring an endoscopic video captured by an endoscope;

detecting a lesion candidate from the endoscopic video;

generating a heat map indicating a possibility of lesion of the lesion candidate in the endoscopic video by a color; and displaying a position of a lesion on a frame of the endoscopic video based on the lesion candidate and the heat map.

DESCRIPTION OF SYMBOLS

1 Endoscopic examination support apparatus
2 Display device
3 Endoscope
11 Processor
12 Memory
13 Interface
21 Lesion detection unit
22 Heat map generation unit
23 Display control unit
100 Endoscopic examination system

The invention claimed is:

1. An endoscopic examination support apparatus comprising:

a memory configured to store instructions; and a processor configured to execute the instructions to:

acquire an endoscopic video captured by an endoscope;

generate a heat map indicating a possibility of lesion by a color, wherein the possibility of lesion is a possibility that an area in the endoscopic video is an area of lesion;

display a set of indicators around the outside of the endoscopic video based on the heat map, wherein the set of indicators includes one indicator representing a longitude position of a lesion and another indicator representing a lateral position of the lesion;

when displaying the position of a single lesion, display the set of indicators on one of left and right end of the frame and one of upper and lower end of the frame; and when displaying the position of multiple lesions, display the set of indicators on both left and right ends of the frame and both upper and lower ends of the frame.

2. The endoscopic examination support apparatus according to claim 1, wherein the processor is further configured to execute the instructions to:

represent the possibility of lesion by a score for each pixel included in a frame image of the endoscopic video, and display the set of indicators in a display mode according to the score.

3. The endoscopic examination support apparatus according to claim 1, wherein the processor is further configured to execute the instructions to:

represent the possibility of lesion by a score for each pixel included in a frame image of the endoscopic video, and calculate an average value of the scores and display the set of indicators in a display mode according to the average value.

4. The endoscopic examination support apparatus according to claim 1, wherein the processor is further configured to execute the instructions to:

represent the possibility of lesion by a score, and display the set of indicators when the score is equal to or larger than a predetermined threshold value.

5. The endoscopic examination support apparatus according to claim 1, wherein, the processor is further configured to execute the instructions to:

display the set of indicators of multiple lesions in different display modes.

6. An endoscopic examination support apparatus according to claim 1, wherein the processor is further configured to execute the instructions to:

use a machine learning model trained in advance, to estimate the lesion included in the endoscopic image.

7. An endoscopic examination support apparatus according to claim 1, wherein the processor is further configured to execute the instructions to:

display an indicator which indicates the position of the lesion in order to support decision making of a doctor.

8. An endoscopic examination support apparatus according to claim 1, wherein the processor is further configured to execute the instructions to display the heat map.

9. An endoscopic examination support apparatus according to claim 1, wherein the processor is further configured to execute the instructions to:

change display mode according to a selection input, the selection selecting from either displaying the set of indicators on one of left or right end of the frame and one of upper or lower end of the frame.

10. An endoscopic examination support method comprising:

acquiring an endoscopic video captured by an endoscope;

generating a heat map indicating a possibility of lesion by a color, the possibility of lesion being a possibility of an area in the endoscopic video being an area of lesion;

displaying a set of indicators around the outside of the endoscopic video based on the heat map, the set of indicators including one indicator representing a longitude position of a lesion and another indicator representing a lateral position of the lesion;

when displaying the position of a single lesion, displaying the set of indicators on one of left and right end of the frame and one of upper and lower end of the frame; and when displaying the position of multiple lesions, displaying the set of indicators on both left and right ends of the frame and both upper and lower ends of the frame.

11. A non-transitory computer-readable recording medium storing a program, the program causing a computer to execute processing comprising:

acquiring an endoscopic video captured by an endoscope;

generating a heat map indicating a possibility of lesion by a color, the possibility of lesion being a possibility of an area in the endoscopic video being an area of lesion;

displaying a set of indicators around the outside of the endoscopic video based on the heat map, the set of indicators including one indicator representing a longitude position of a lesion and another indicator representing a lateral position of the lesion;

when displaying the position of a single lesion, displaying the set of indicators on one of left and right end of the frame and one of upper and lower end of the frame; and when displaying the position of multiple lesions, display-ing the set of indicators on both left and right ends of the frame and both upper and lower ends of the frame.

* * * * *